(12) United States Patent
Radovic

(10) Patent No.: US 7,276,244 B2
(45) Date of Patent: Oct. 2, 2007

(54) METHODS OF TREATING ABNORMALITIES OF THE FIRST METATARSOPHALANGEAL JOINT OF THE FOOT

(75) Inventor: Philip Radovic, 665 Camino de los Mares, Suite 304, San Clemente, CA (US) 92673

(73) Assignee: Philip Radovic, San Clemente, CA (US)

( * ) Notice: Subject to any disclaimer, the term of this patent is extended or adjusted under 35 U.S.C. 154(b) by 0 days.

(21) Appl. No.: 11/056,382

(22) Filed: Feb. 11, 2005

(65) Prior Publication Data
US 2005/0202047 A1  Sep. 15, 2005

Related U.S. Application Data

(60) Provisional application No. 60/544,017, filed on Feb. 12, 2004.

(51) Int. Cl.
*A61K 39/08* (2006.01)
*A61K 39/02* (2006.01)

(52) U.S. Cl. ............... 424/239.1; 424/236.2; 424/9.1; 514/2; 514/12; 530/350; 435/252.7

(58) Field of Classification Search ............ 424/239.1, 424/236.1, 9.1; 514/2, 12; 530/350; 435/252.7
See application file for complete search history.

(56) References Cited

U.S. PATENT DOCUMENTS

| | | | |
|---|---|---|---|
| 4,932,936 | A | 6/1990 | Dykstra et al. |
| 5,053,005 | A | 10/1991 | Borodic et al. |
| 5,766,605 | A | 6/1998 | Sanders et al. |
| 6,087,327 | A | 7/2000 | Pearce et al. |
| 6,290,961 | B1 | 9/2001 | Aoki et al. |
| 6,319,505 | B1 | 11/2001 | Aoki et al. |
| 6,333,037 | B1 | 12/2001 | Aoki et al. |
| 6,632,433 | B2 | 10/2003 | Aoki et al. |
| 2003/0224020 | A1 | 12/2003 | Zabudkin et al. |
| 2005/0123567 | A1* | 6/2005 | First .................. 424/239.1 |

FOREIGN PATENT DOCUMENTS

WO    WO 95/17904 A    7/1995

OTHER PUBLICATIONS

Sherman A L, Willick S P, Cardenas D D , "Management of Focal Dystonia of the Extensor Hallucis Longus Muscle with Botulinum Toxin Injection: A Case Report," Arch Phys Med Rehabil, 1998, 1303-1305, 79.
Yelnik A P, Colle F M, Bonan I V, Lamotte D R, "Disabling Overactivity of the Extensor Hallucis Longus after Stroke: Clinical Expression and Efficacy of Botulinum Toxin Type A," Arch Phys Med Rehabil, 2003, 147-149, 84.
Yelnik AP, Bonan I V: "Post Stroke Hemiplegia: Lower Limb Benefit from Botulinum Toxin (Review)," Annales De Réadaptation Et De Médecine Physique, 2003, 281-284, 46.
Ferrari J: "Bunions," Clin Evid., 2003, 1259-1270, 10.
Koman, et al., "Botulinum Toxin Type A Neuromuscular Blockade in the Treatment of Equinus Foot Deformity in Cerebral Palsy: A Multicenter, Open-Label Clinical Trial," Pediatrics 2001; 108; 1062-1071 [online] [retrieved on May 10, 2005]<URL: www.pediatrics.org>.
Ubhi, T. et al., "Randomised Double Blind Placebo Controlled Trial of the Effect of Botulinum Toxin on Walking in Cerebral Palsy," Arch. Dis. Child. Dec. 2000; 83:481-487, Downloaded on Apr. 12, 2003 from website: http://adc.bmj.com.
Tamura, B M. et al., "Plantar Hyperhidrosis and Pitted Keratoloysis Treated with Botulinum Toxin Injection," Dermatol Surg. 30(12 Pt 2): 1510, 2004. Abstract downloaded on May 1, 2006 from website: http://www.ncbi.nlm.nih.gov.
Suputtitada, A., "Local Botulinum Toxin Type A Injections in the Treatment of Spastic Toes," Am. J. Phys. Med. Rehabil 81(10);770, 2002.
Simpson, LL., "Current Concepts on the Mechanism of Action of Clostridial Neurotoxins," Das Gupta BR (ed): Botulinum and Tetanus Neurotoxins. New York, Plenum Press: 5, 1993.
Sherman, A L. et al., "Management of Focal Dystonia of the Extensor Hallucis Longus Muscle with Botulinum Toxin Injection: A Case Report," Arch Phys Med Rehabil, 1998, 1303-1305, 79.
Placzek, R. et al., "Botulinum Toxin A in Orthopedic Pain Therapy," Schmerz 18(6):498, 2004. Abstract downloaded on May 1, 2006 from website: http://www.ncbi.nlm.nih.gov.
Hoffmeyer, P. et al., "Muscle is Hallux Valgus," Clin Orthop Relat Res. , Jul. 1988; (232):112-8. Abstract downloaded on Jan. 8, 2007 from website: http://www.ncbi.nlm.nih.gov.
Hambleton, P. et al., "Botulinum Neurotoxins: Origin, Structure, Molecular Actions and Antibodies," Moore AP, ed. Handbook of Botulinum Toxin Treatment, Oxford: Blackwell Science Ltd: 16, 1995.
Giladi, N. et al., "The Use of Botulinum Toxin to Treat "Striatal" Toes," J Neurol Neurosurg Psychiatry, 1994.
Ferrari J., "Interventions for Treating Hallux Valgus (Abductovalgus) and Bunions," Cochrane Database Syst. Rev. 2004; (1): CD000964. Downloaded on Aug. 3, 2006 from website: http://www.ncbi.nlm.nih.gov.
Biglan, A W. et al. "Management of Strabismus with Botulinum Toxin," A. Ophthalmology 96:935-43, 1989. Abstract downloaded from website: http://www.ncbi.nlm.nih.gov.
Bhidayasiri, R. et al., "Expanding Use of Botulinum Toxin," J. Neurol. Sci. 235(1-2):1, 2005. Abstract downloaded on May 1, 2006 from website: http://www.ncbi.nlm.nih.gov.

(Continued)

*Primary Examiner*—Chih-Min Kam
(74) *Attorney, Agent, or Firm*—Knobbe, Martens, Olson & Bear LLP

(57) ABSTRACT

Disclosed is a method for treating abnormalities of the first metatarsophalangeal joint of the foot of a mammal comprising administering a therapeutically effective amount of neuromuscular toxin to the mammal. Preferred embodiments include administering toxins capable of interfering with the connection between muscle and nerve, e.g. botulinum toxin, to the patient to treat such abnormalities as hallux abductovalgus, hallux varus, hallux limitus, and hallux rigidus.

22 Claims, No Drawings

OTHER PUBLICATIONS

Babcock, M S. et al., "Treatment of Pain Attributed to Plantar Fasciitis with Botulinum Toxin A: A Short-Term, Randomized, Placebo-Controlled, Double-Blind Study," Am. J. Phys. Med. Rehabil. 84(9):649, 2005. Abstract downloaded on May 1, 2006 from website: http://www.ncbi.nlm.nih.gov.

Arinci, Incel N. et al., "Muscle Imbalance in Hallux Valgus: An Electromyographic Study," Am. J. Phys. Med. Rehabil., May 2003; 82(5):345-9. Abstract downloaded on Jan. 8, 2007 from website: http://www.ncbi.nlm.nih.gov.

Aoki, K R., "Evidence for Antinociceptive Activity for Botulinum Toxin Type A in Pain Management," Headache Jul. 2003; 43 Suppl 1:S9-15. Abstract downloaded on May 1, 2006 from website: http://www.ncbi.nlm.nih.gov.

PCT International Search Report and Written Opinion mailed Oct. 11, 2005.

PCT Written Opinion of the International Examining Authority mailed Oct. 3, 2006.

* cited by examiner

METHODS OF TREATING ABNORMALITIES OF THE FIRST METATARSOPHALANGEAL JOINT OF THE FOOT

This application claims priority to U.S. Provisional Application Ser. No. 60/544,017, which was filed on Feb. 12, 2004 and is hereby incorporated in its entirety.

FIELD OF THE INVENTION

The present invention relates to methods of treating abnormalities of the first metatarsophalangeal joint of the foot.

BACKGROUND OF THE INVENTION

Abnormalities of the first metatarsophalangeal joint encompass a variety of disorders, including hallux abductovalgus (commonly known as "bunions"), hallux varus, hallux limitus, hallux rigidus, and other disorders.

Hallux abductovalgus ("hallux abductovalgus") is one of the most frequently seen abnormalities of the first metatarsophalangeal joint. In a patient with hallux abductovalgus, the proximal phalanx of the hallux (the great toe) points toward the second toe. This results in a lateral deviation of the great toe (tilting of the great toe away from the mid-line of the body) and a widening of the angle between the first and second metatarsals.

One of the greatest deforming forces in the development of hallux abductovalgus is the adductor hallucis muscle. This muscle has two muscle bellies, a transverse and an oblique. In a patient with hallux abductovalgus, the adductor hallucis muscle gains mechanical advantage, pulling the hallux laterally and forcing the metatarsal head medially.

The severity of hallux abductovalgus deformities has traditionally been quantified based on a variety of measurements from radiographs. One common measurement is the intermetatarsal angle between the line of the first and second metatarsal. Normally, this angle can average from about 6 to about 8 degrees. In a patient with hallux abductovalgus, the intermetatarsal angle is increased, with severe abnormalities measuring greater than 30 degrees. Another common measurement is the hallux abductus angle, which is the angle between the longitudinal axes of the first metatarsal and the great toe. Normally, this angle can average from about 10 to about 15 degrees. In hallux abductovalgus, the hallux abductus angle is increased, with extreme cases measuring greater than 70 degrees. A third common measurement is the tibial sesamoid position. With hallux abductovalgus, the first metatarsal deviates medially off of the sesamoids, causing apparent lateral dislocation. The position of the tibial sesamoid in relation to a line drawn through the mid-longitudinal axis of the first metatarsal determines the tibial sesamoid position.

Hallux varus is an abnormality of the first metatarsophalangeal joint in which the proximal phalanx of the hallux (great toe) points away from the second toe. This results in a medial deviation of the great toe (tilting of the great toe toward the mid-line of the body). A common deforming force in the development of hallux varus is the abductor hallucis muscle. In a patient with hallux varus, the abductor hallucis muscle can gain mechanical advantage, pulling the hallux medially and forcing the metatarsal head laterally.

Hallux limitus is an abnormality of the first metatarsophalangeal joint that results in a restricted range of motion in the first metatarsophalangeal joint. Normally, the range of motion in the first metatarsophalangeal joint can average from about 55 to about 75 degrees. In a patient with hallux limitus, this range of motion is decreased. When the range of motion becomes less than about 5 degrees, this condition is commonly referred to as hallux rigidus (stiff great toe).

Hallux limitus can be functional or structural. Functional hallux limitus exhibits a restricted range of motion in the first metatarsophalangeal joint only during weightbearing. Structural hallux limitus, on the other hand, exhibits a restricted range of motion in the first metatarsophalangeal joint both during weightbearing and non-weightbearing.

SUMMARY OF THE INVENTION

According to the present invention, a variety of abnormalities of the first metatarsophalangeal joint can be treated using neuromuscular toxins. For example, in one embodiment, hallux abductovalgus can be treated by administering to the patient an amount of toxin sufficient to alleviate a symptom of hallux abductovalgus. In preferred aspects, the toxin can be administered by intramuscular injection, preferably into the adductor hallucis muscle. Most preferably, toxin can be injected into both of the two muscle bellies of the adductor hallucis: the transverse and the oblique. In addition, toxin can be administered to the extensor digitorum brevis muscle, which is involved in extension of the great toe.

In another embodiment, hallux varus can be treated by administering an amount of toxin sufficient to alleviate a symptom of hallux varus. In preferred aspects, the toxin can be administered by intramuscular injection, preferably into the abductor hallucis muscle.

In another embodiment, hallux limitus (or in severe cases, hallux rigidus) can be treated by administering an amount of toxin sufficient to increase the range of motion in the first metatarsophalangeal joint. In preferred aspects, the toxin can be administered by intramuscular injection, preferably into the flexor hallucis brevis muscle. Most preferably, toxin can be injected into both the medial and lateral muscle bellies of the flexor hallucis brevis muscle.

Other abnormalities of the first metatarsophalangeal joint which can be treated in accordance with the present invention can include trauma, sesamoid disorders, and other disorders of the first metatarsophalangeal joint.

The toxin can be any neuromuscular toxin capable of interfering with the connection between muscle and nerve. In preferred aspects, the neuromuscular toxin is an inhibitor of acetylcholine release. For example, a clostridial toxin, such as botulinum toxin, preferably can be used. Currently, there are seven known serotypes of botulinum toxin, designated as types A through G. The most currently preferred neuromuscular toxin currently is botulinum toxin type A.

As described above, the preferred technique for administering the toxin is by intramuscular injection. For example, in preferred aspects of this embodiment, a needle can be inserted into the target muscle and the toxin injected into the muscle, repeating as necessary to deliver the desired amount of toxin to the muscle. In further preferred aspects of this embodiment, electrical stimulation can be used to determine the optimal sites for injection. Other methods of administering the toxin can also be used.

In another embodiment, the method optionally further comprises stimulating the muscle opposed to the muscle to which the toxin has been administered.

In another embodiment, the method optionally further comprises immobilizing the foot to maintain position after the toxin has been administered. It is further contemplated that post procedural immobilization can be used in conjunction with electrical stimulation of the opposing muscle.

In another embodiment, the toxin can be administered to the patient while undergoing surgery on the foot.

DETAILED DESCRIPTION OF THE INVENTION

The present invention relates to methods of treating abnormalities of the first metatarsophalangeal joint through the use of neuromuscular toxins. Practice of the invention involves administering to the patient an amount of toxin sufficient to alleviate a symptom of the joint abnormality. In preferred aspects, the toxin can be administered by intramuscular injection. Injection of small doses of neuromuscular toxin into the muscle induces an effect similar to denervation, resulting in dose-dependent loss of muscle tone and subsequent muscle atrophy.

The toxin can be any neuromuscular toxin capable of interfering with the connection between muscle and nerve. In preferred aspects, the toxin is an inhibitor of acetylcholine release, such as botulinum toxin or a protein that mimics its acetylcholine release inhibiting effect. Currently, there are seven known serotypes of botulinum toxin, designated as types A through G. Other potentially useful toxins include, but are not limited to, tetanus toxins, tetrodotoxin, difficile toxins, butyricum toxins, and various animal venoms. Staphylococcal alpha-toxin can also be used, as it has also been shown to induce reversible, flaccid paralysis of skeletal muscle. (Harshman, et al., Infect. Immun., 62:421-425, 1994).

Recombinant, synthetic, and derivative neuromuscular toxins are also contemplated by the invention. For example, proteins produced using recombinant DNA technology which mimic the effects of these natural toxins can be used. Suitable toxins can also include proteins synthetically produced using in vitro protein synthesizing techniques well known in the art. Synthetically produced neurotoxins are also intended to include substances which have been rendered neurotoxic by a variety of manipulations, such as enzymatic or chemical processing and conjugation or derivatization with moieties which themselves are neurotoxic. Accordingly, toxins for use in connection with the present invention include derivatives of naturally occurring toxins and other known toxins. "Derivative" means a chemical entity which is slightly different from a parent chemical entity but which still has a biological effect similar, or substantially similar, to the biological effect of the chemical entity. For example, suitable toxin derivatives can include neurotoxin components that have modified amino acid side chains, as is well known in the art.

The invention also contemplates that derivatives in the form of fragments, subunits, and chimeras of neuromuscular toxins can be used. Botulinum toxin, for example, is composed of a heavy chain and a light chain, joined together by two disulfide bonds. Through disruption of the disulfide bond, the subunits can be separated and combined with other moieties, such as stabilizers or toxicity enhancers. If re-associated with other subunits or toxic substances, a biologically active chimera suitable for use in the present invention can be produced. Toxin fragments, e.g., a portion (s) of neurotoxin that retains neurotoxic and/or biological activity, can also be used.

The invention also contemplates that neurotoxic substances that share amino acid sequence homologies and/or identities with currently known neuromuscular toxins can be used. In addition, mixtures of toxins can also be used, preferably where such mixtures have been selected to cause longer-lasting action than with a single toxin.

The currently preferred toxin is a botulinum toxin, most preferably botulinum toxin type A. Commercially available from Allergan (BOTOX) and Ipsen (DYSPORT), botulinum toxin type A is an artificially produced neuromuscular paralyzing agent that is currently licensed by the FDA for cervical dystonia, blepharospasm, strabismus, and wrinkles. When injected into muscle, the botulinum toxin binds to the nerve ending and blocks the nerve from releasing acetylcholine. As a result, the muscle cannot contract and effectively relaxes. Botulinum toxin type B is commercially available under the trademark MYOBLOC and has also been shown to be clinically safe and effective in treating a number of neuromuscular conditions. Use of botulinum toxin type F is also being investigated for commercialization.

The degree of muscle relaxation can be regulated by variation of dosage, variation in the method or site of administration, and frequency of administration.

The dose of toxin administered to the patient will depend upon the severity of the condition (e.g. the size of the area requiring treatment, the age and size of the patient and the potency of the toxin). One unit (U) of toxin is defined as the $LD_{50}$ upon intraperitoneal injection into female Swiss Webster mice weighing 18 to 20 grams each. Typically, the dose administered to the patient may be from about 1 to about 1000 units. In one embodiment, the currently preferred dosage for botulinum toxin type A is from about 50 units to about 300 units. Although such a maximum far exceeds the dosage employed in the treatment of blepharospasms and dystonias (10-150 U), it is well below the lethal dose for humans (estimated to be about 3000 U). Most preferably, the range of dosage of botulinum toxin type A is from about 75 units to about 100 units. Those of ordinary skill in the art will know of or can readily determine without undue experimentation suitable dosages for other neuromuscular toxins.

Because the effects of neuromuscular toxins can be delayed, it is further contemplated that post procedural monitoring of the patient can be used to determine if further administration of the toxin is needed. For example, in the case of hallux abductovalgus, comparison of pre and post procedural measurements of the intermetatarsal angle, the hallux abductus angle, and/or the tibial sesamoid position can be used to determine whether further treatment is required. In a currently preferred aspect of this embodiment, such post procedural monitoring of the patient can be performed at about 3 to 6 weeks following the initial procedure. If such monitoring reveals that further treatment is required, toxin can be readministered as needed.

The effects of botulinum toxin A generally last for about 3 to about 6 months, depending on the patient. If symptoms recur, toxin can be readministered as needed. Frequency of administration for other neuromuscular toxins can be determined using routine experimentation by those skilled in the art.

As described above, the preferred method of administering the selected toxin is by injection into the target muscle. Intramuscular injection can be accomplished using any suitable injection device. For example, a 27-gauge needle in a 3-cc tuberculin syringe can be used to deliver the toxin directly into the muscle. Needle-less injection systems can also be used to inject the toxin into the target muscle.

Alternatively, those of ordinary skill in the art will be able to determine other suitable techniques for administering the toxin. For example, transdermal delivery systems can be used to administer the toxin as needed. In addition, the toxin can be administered during surgery on the foot, in which case any suitable technique for delivering the toxin to the target area during surgery can be used.

If administered by intramuscular injection, those of ordinary skill in the art will be able to determine suitable techniques for injecting the toxin. In currently preferred aspects of this embodiment, electrical stimulation can be used to determine the optimal sites for injection. For example, an injectable needle attached to an electrode can be inserted through the skin and into the target muscle. This needle electrode can then be attached to the stimulator probe of a standard electrical stimulation unit. As the needle is advanced into the muscle, electrical stimulation is delivered to elicit a motor response. As the stimulated muscle responds by contracting, visual identification can be used to confirm that the needle is properly located in the target muscle.

For example, if toxin is to be administered by intramuscular injection to treat hallux varus, the abductor hallucis muscle preferably can be palpated at the medial aspect of the foot and the needle electrode placed from the medial skin directed into the mid belly of the abductor hallucis muscle. Once a motor response is elicited (hallux adduction), the toxin can be injected.

Those of ordinary skill in the art will know of, or can readily ascertain, other suitable techniques for injecting the toxin, if intramuscular injection is to be used. For example, depending on the muscle to be injected, electromyography can be used, alone or in combination with electrical stimulation, to determine the optimal sites for injection. Alternatively, those of ordinary skill in the art may be able to determine the optimal sites of injection anatomically. In addition, those of ordinary skill will appreciate that in some cases there may be reasons to administer the toxin to suboptimal sites. In each case, this process can be repeated as necessary to deliver sufficient toxin to the target area.

In another embodiment, the method optionally further comprises stimulating the muscle opposed to the muscle to which the toxin is administered. In most cases, such further stimulation is unnecessary. When used, stimulation of the opposing muscle can be achieved by using a standard electric muscle stimulator to deliver electronic impulses to the opposing muscle. For example, in the case of hallux abductovalgus, stimulation can be applied by placing electrode pads preferably over the motor points of the abductor hallucis and delivering low volt stimulation to cause a muscle contraction. Most preferably, stimulation of the opposing muscle can be performed by the patient as needed following administration of the neuromuscular toxin. For example, in currently preferred aspects of this embodiment, the patient can be instructed to stimulate the opposing muscle on a daily basis before coming in for follow-up.

In another embodiment, the method optionally further comprises immobilizing the foot to maintain position after the toxin has been administered. The use of immobilization to maintain position following corrective procedures for abnormalities of the first metatarsophalangeal joint is well known in the art. For example, a splint, surgical shoe, ridged sole shoe, casting, gauze, tape, or the like can be used to immobilize to foot following administration of the toxin. In a currently preferred aspect of this embodiment, a standard splint can be placed on the foot after the toxin has been administered. For example, in the case of hallux abductovalgus, the patient preferably can be instructed to place the foot in a bunion splint on a nightly basis before coming in for follow-up.

In another embodiment, immobilization can be used in conjunction with electrical stimulation of the opposing muscle. For example, in the case of hallux abductovalgus, the patient preferably can be instructed to stimulate the abductor hallucis muscle while placing the foot in a bunion splint on a daily basis before coming in for follow-up.

In another embodiment, the toxin can be administered to the patient during surgery on the patient's foot. In preferred aspects, toxin can be administered to the target muscle during surgery for the joint abnormality, preferably after the primary surgical treatment has been carried out. For example, in the case of hallux abductovalgus, the toxin preferably can be administered by intramuscular injection into the adductor hallucis muscle during surgery on the first metatarsophalangeal joint, preferably after the primary surgical treatment has been carried out.

EXAMPLES

The invention will now be illustrated by reference to the following nonlimiting examples.

In each example, appropriate areas were injected with a sterile solution containing Botulinum toxin (e.g. 100 units BOTOX solubilized in 0.9% sterile saline without preservative). Determination of the site to inject was performed using a DIGISTIM III peripheral nerve/muscle stimulator and an INOJECT needle electrode, with placement of the lead (gel electrode) in the patient's thigh.

Example 1

A female patient suffering from hallux abductovalgus was treated with 100 units of botulinum toxin type A by direct injection of the toxin into the adductor hallucis muscle. Determination of the injection sites was performed by placing the INOJECT needle from the dorsal mid first interspace of the foot proximal to the first and second metatarsophalangeal joint and delivering a 2 Hz pulse while advancing the needle in the direction of the transverse adductor hallucis muscle belly. Once a motor response was elicited (pulsating abduction of the hallux), 25 units of the toxin were injected into the transverse belly of the adductor hallucis muscle. The needle was then partially retracted and redirected upward toward the oblique arm of the adductor hallucis muscle and advanced plantarly until a motor response was elicited (adduction of the hallux). At this point, 75 units of the toxin were injected into the oblique adductor hallucis muscle. Within 1 week, the symptoms of hallux abductovalgus were markedly reduced.

The patient was followed for 41 days following injection, with pre and post procedure measurements of radiographs obtained to monitor the patient's progress. Before the procedure, the patient exhibited an intermetatarsal angle of 14 degrees, a tibial sesamoid position of 4, and a hallux abductus angle of 20 degrees. Twenty four days following injection, the patient's intermetarsal angle was reduced to 10 degrees, her tibial sesamoid position was 3, and her hallux abductus angle was 10 degrees. Forty one days following injection, the patient's intermetarsal angle was further reduced to 9 degrees, her tibial sesamoid position was 2, and her hallux abductus angle was 7 degrees. Through day 41, the patient has reported none of her previous symptoms associated with hallux abductovalgus.

Example 2

A female patient suffering from hallux limitus was treated with 100 units of botulinum toxin type A by direct injection of the toxin into the flexor hallucis brevis muscle. Determination of the injection sites was performed by placing the INOJECT needle through the skin from the dorsum of the foot at the mid first interspace proximally and applying stimulation while advancing the needle in a plantar medial direction to the lateral belly of the flexor hallucis brevis.

Once location was confirmed with a motor response of plantar flexion of the first metatarsophalangeal joint, 50 units of toxin were injected into the lateral belly of the flexor hallucis brevis muscle. The medial belly of the flexor hallucis brevis muscle was then approached with the needle through the medial aspect of the foot where the muscle can be palpated. The needle was advanced transversely from about the level of the first metatarsal until a motor response of plantar flexion of the first metatarsophalangeal joint was elicited. At this point, 50 units of toxin were injected into the medial belly of the flexor hallucis brevis muscle.

Within 3 days, the symptoms of hallux limitus were markedly reduced. Before treatment, the patient exhibited a range of motion at the first metatarsophalangeal joint of 30 degrees with pain upon range of motion. One week after injection, the patient exhibited a range of motion of 50 degrees at the first metatarsophalangeal joint with no pain at the end range of motion. At week 6, the patient exhibited a range of motion of 55 degrees at the first metatarsophalangeal joint with no pain upon range or end range of motion.

While particular forms of the invention have been described, it will be apparent that the invention can be embodied in other specific forms without departing from the spirit and scope thereof.

What is claimed is:

1. A method for treating abnormalities of the first metatarsophalangeal joint of the foot of a mammal, wherein the joint abnormality is selected from the group consisting of hallux abductovalgus, hallux varus, hallux limitus, or hallux rigidus, comprising administering an amount of a botulinum toxin to the adductor hallucis muscle, abductor hallucis muscle, or flexor hallucis brevis muscle, sufficient to alleviate a symptom of the joint abnormality.

2. The method of claim 1 wherein the joint abnormality is hallux abductovalgus.

3. The method of claim 2 wherein the botulinum toxin is administered to the adductor hallucis muscle.

4. The method of claim 1 wherein the joint abnormality is hallux varus.

5. The method of claim 4 wherein the botulinum toxin is administered to the abductor hallucis muscle.

6. The method of claim 1 wherein the joint abnormality is hallux limitus.

7. The method of claim 6 wherein the botulinum toxin is administered to the flexor hallucis brevis muscle.

8. The method of claim 1 wherein the joint abnormality is hallux rigidus.

9. The method of claim 8 wherein the botulinum toxin is administered to the flexor hallucis brevis muscle.

10. The method of claim 1 wherein the botulinum toxin is administered by intramuscular injection.

11. The method of claim 10 wherein electrical stimulation is used to determine the optimal site or sites for injection.

12. The method of claim 1 wherein the botulinum toxin is botulinum toxin type A.

13. The method of claim 12 wherein the botulinum toxin type A is administered in amount of between about 50 units and about 300 units.

14. The method of claim 1 wherein the botulinum toxin is botulinum toxin type B.

15. The method of claim 1 wherein the botulinum toxin is a mixture of toxins.

16. The method of claim 1 wherein a symptom of the joint abnormality is alleviated for at least 3 months.

17. The method of claim 1 additionally comprising readministering the botulinum toxin.

18. The method of claim 1 additionally comprising immobilizing the foot to maintain position after the toxin has been administered.

19. The method of claim 1 additionally comprising stimulating a muscle opposed to the muscle to which the toxin is administered.

20. The method of claim 1 wherein administration of the botulinum toxin is carried out during surgery on the foot.

21. The method of claim 1 wherein the mammal is a human.

22. The method of claim 1, wherein the botulinum toxin is selected from the group consisting of types A, B, C1, D, E, F and G.

* * * * *